United States Patent [19]
Nelson et al.

[11] Patent Number: 5,972,958
[45] Date of Patent: Oct. 26, 1999

[54] 4-AMINOALKOXY-1,3-DIHYDRO-BENZOIMIDAZOL-2-THIONES

[75] Inventors: James Albert Nelson, Washington Crossing, Pa.; Richard Eric Mewshaw, Princeton; Uresh Shantilal Shah, Cranbury, both of N.J.

[73] Assignee: American Home Products Corporation, Madison, N.J.

[21] Appl. No.: 09/025,011

[22] Filed: Feb. 17, 1998

Related U.S. Application Data

[60] Provisional application No. 60/038,423, Feb. 18, 1997.

[51] Int. Cl.$^6$ .................. A61K 31/415; A61K 31/47; C07D 401/12; C07D 235/28
[52] U.S. Cl. .................. 514/307; 514/387; 546/148; 548/304.7; 548/307.1
[58] Field of Search ...................... 514/387, 307; 548/304.7, 307.1; 546/148

[56] References Cited

U.S. PATENT DOCUMENTS 4,140,789  2/1979  Jaeggi ........................ 424/248.55

FOREIGN PATENT DOCUMENTS

| 0707007 | 4/1996 | European Pat. Off. . |
| WO8601204 | 2/1986 | WIPO . |
| WO9723216 | 7/1997 | WIPO . |

OTHER PUBLICATIONS

Jaen J.C. et al., Journal of Med. Chem., vol. 31, No. 8 (Aug. 1988) p 1621–1625.
Staehelin et al., J. Biological Chemistry 258 (6) 3496–3502, 1983.

*Primary Examiner*—Laura L. Stockton
*Attorney, Agent, or Firm*—Rebecca R. Barrett

[57] ABSTRACT

This invention relates to a novel series of compounds having potency at the dopamine $D_2$ receptor which are illustrated by the following Formula I:

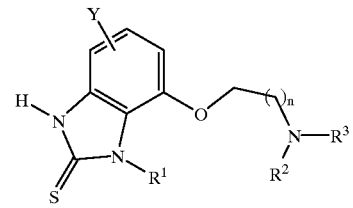

wherein:

$R^1$ is hydrogen or $C_1$–$C_6$ alkyl;

$R^2$ is hydrogen or $C_1$–$C_6$ alkyl;

$R^3$ is selected from hydrogen, straight-chain and branched alkyl group having up to 10 carbon atoms, cyclohexylmethyl or —$(CH_2)_m$Ar where Ar is phenyl, naphthyl, thienyl, furanyl or pyridinyl, each optionally substituted by one or two substituents selected independently from $C_1$–$C_6$ alkyl, halogen, $C_1$–$C_6$ alkoxide, trifluoromethyl, 4-fluorobutyrophenone;

or $NR^2R^3$ is 1, 2, 3, 4-tetrahydroquinolin-1-yl or 1, 2, 3, 4-tetrahydroisoquinolin-2-yl;

m is 1–5;

n is 1 or 2;

Y is halogen, $C_1$–$C_6$ alkyl, and $C_1$–$C_6$ alkoxy; or a pharmaceutically acceptable salt thereof.

26 Claims, No Drawings

4-AMINOALKOXY-1,3-DIHYDRO-BENZOIMIDAZOL-2-THIONES

This application claims benefit of priority to provisional application No. 60/038,423 filed Feb. 18, 1997.

FIELD OF THE INVENTION

This invention relates to a novel series of compounds having potency at the dopamine $D_2$ receptor which are illustrated by the following Formula I:

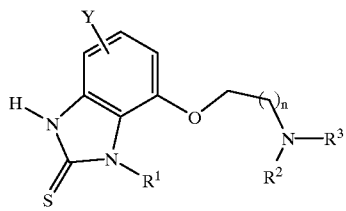

BACKGROUND OF INVENTION

Efforts to induce antipsychotic activity with dopamine autoreceptor agonists have been successful (Dorsini et al., Adv. Biochem. Psychopharmacol., 16, 645–648, 1977; Tammninga et al., Science, 200, 567–568, 1975; and Tamminga et al., Psychiatry, 398–402, 1986). A method for determining intrinsic activity at the dopamine $D_2$ receptor was recently reported (Lahti et al., Mol. Pharm., 42, 432–438, 1993) Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

In accordance with this invention, there is provided a group of compounds which are useful antipsychotic agents essentially free from extrapyramidal side effects (EPS). The compounds of this invention are dopamine agonists with various degrees of intrinsic activity some of which are selective autoreceptor agonists, and therefore partial agonist (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing a well as inhibition of dopamine synthesis and release and therefore provide a means of controlling hyperactivity of the dopaminergic systems. The compounds of this invention were also found to have high intrinsic activity and therefore they can behave as the natural neurotransmitter, i.e., as full agonists. As such, they are useful in the treatment of diseases having abnormal concentrations of dopamine and could be used as dopamine surrogates possibly in the treatment of Parkinson's disease.

A literature search indicated a series of benzimidazole-2-ones have been prepared as described in German Patent 2700193. In particular, CGP-12177 (Ciba Geigy, shown below) was found to be a β-adrenergic receptor antagonist [J. Biol. Chem., 258, 3496–3502, 1983].

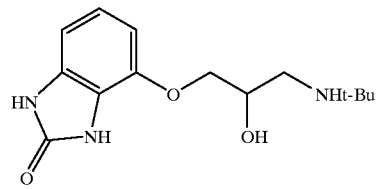

BRIEF DESCRIPTION OF THE INVENTION

The compounds of this invention are 4-aminoethoxy-1,3-dihydro-benzoimidazol-2-thiones which are illustrated by Formula I

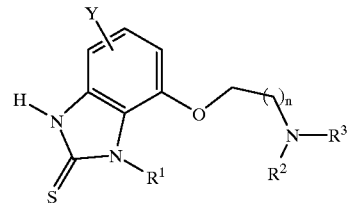

wherein:

$R^1$ is hydrogen or $C_1$–$C_6$ alkyl;

$R^2$ is hydrogen or $C_1$–$C_6$ alkyl;

$R^3$ is selected from hydrogen, straight-chain and branched alkyl group having up to 10 carbon atoms, cyclohexylmethyl and —$(CH_2)_m$Ar where Ar is phenyl, naphthyl, thienyl, furanyl or pyridinyl, each optionally substituted by one or two substituents selected independently from $C_1$–$C_6$ alkyl, halogen, $C_1$–$C_6$ alkoxy, or trifluoromethyl, or or $NR^2R^3$ is 1, 2, 3, 4-tetrahydroquinolin-1-yl or 1, 2, 3, 4-tetrahydroisoquinolin-2-yl;

m is 1–5;

n is 1 or 2;

Y is halogen, $C_1$–$C_6$ alkyl, or $C_1$–$C_6$ alkoxy;

and the pharmaceutically acceptable salts thereof.

Pharmaceutically acceptable acid addition salts have the utility of the free base. Such salts are prepared by methods well known to the art are formed with both inorganic or organic acids including but not limited to fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

DETAILED DESCRIPTION OF THE INVENTION

The compounds of Formula I are generally prepared by the overall sequence indicated in the following Schemes I–III. Scheme I depicts the synthesis of invention compounds where one of $R^1$ or $R^2$ is hydrogen.

Scheme I

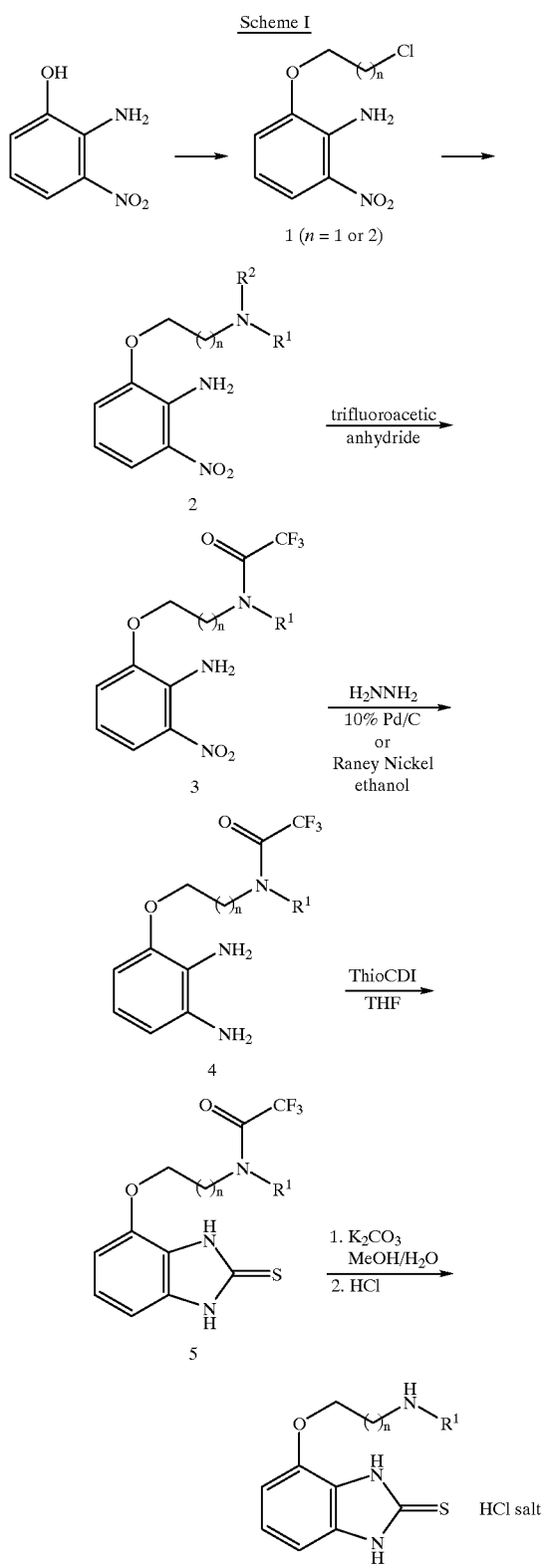

Scheme II outlines the synthesis of an invention compound where neither of R¹ and R² are hydrogen.

Scheme II

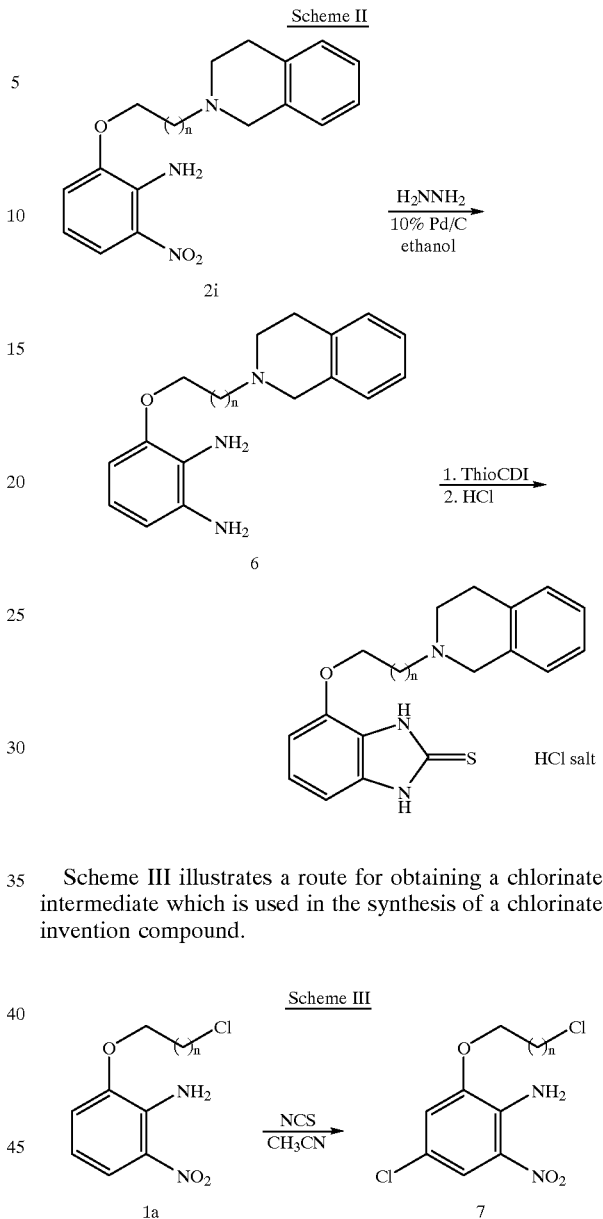

Scheme III illustrates a route for obtaining a chlorinated intermediate which is used in the synthesis of a chlorinated invention compound.

The following synthetic procedures for intermediates and invention products are included for illustrative purposes only and are should not be construed as limiting to this disclosure. Those skilled in the art of organic synthesis may be aware of other preparative methods for preparing the intermediates and invention compounds. The reagents and starting materials used are either commercially available or can be prepared according to standard literature procedures.

INTERMEDIATE 1a (n=1)

2-(2-Chloroethoxy)-6-nitro-phenylamine

Method 1.

To a solution of 2-amino-3-nitrophenol (5.0 g, 32.4 mmol), triphenylphosphine (12.8 g, 48.7 mmol) and 2-chloroethanol (3.9 g, 48.7 mmol) in tetrahydrofuran (120 mL) at 0–5° C. was added over 30 min a solution of diethyl azodicarboxylate (8.5 g, 48.7 mmol) in tetrahydrofuran (75 mL). The mixture was warmed to 23° C. and stirred for 18 hr. The solvent was removed under vacuum to give a dark brown oil. Purification by chromatography (1.3 kg silica gel, 30% hexane—ethyl acetate) afforded 3.1 g (44.2%) of an orange solid, mp 71–73° C.; MS (+)PBEI m/e 216/218 (M$^+$).

Elemental analysis for $C_8H_9ClN_2O_3$: Calc'd: C, 44.36; H, 4.19; N, 12.93; Found: C, 44.45; H, 4.02; N, 12.97

Method 2.

A slurry containing 2-amino-3-nitrophenol (32.0 g, 0.208 mol), 1,2-dichloroethane (260.0 g, 2.65 mol), potassium carbonate (35.0 g, 0.252 mol) and 2-butanone (750 mL) was refluxed for 24 hr. The mixture was cooled, filtered and the solids were washed with ethyl acetate. The filtrate was concentrated to an oily residue that was dissolved in ethyl acetate (500 mL). The organic layer was washed with 1 N sodium hydroxide (250 mL), water (500 mL), and brine (2× 500 mL), dried over anhydrous magnesium sulfate. Concentration of the filtered solution and trituration of the residue with hexane afforded 37.8 g (84.6%) of product as an orange solid, mp 71–73° C.; MS (+)PBEI m/e 216/218 (M$^+$).

INTERMEDIATE 1b (n=2)

2-(3-Bromo-propoxy)-6-nitro-phenylamine

Following the procedure of method 2 above and substituting 1,3-dibromopropane for 1,2-dichloroethane, the title compound is obtained as a yellow solid, (78.7%) mp 88–89° C.; MS EI m/e 274/276 (M$^+$).

Elemental analysis for $C_9H_{11}BrN_2O_3$: Calc'd: C, 39.29; H, 4.03; N, 10.18; Found: C, 39.71; H, 3.91; N, 10.27

INTERMEDIATE 2a 2-(2-Benzylamino-ethoxy)-6-nitro-pheenylamine

A mixture of 2-(2-chloroethoxy)-6-nitro-phenylamine (3.0 g, 13.8 mmol) and benzylamine (9.0 g, 84.0 mmol) was heated at 100–110° C. for 6 hr. The excess benzylamine was removed by distillation under vacuum (70–75° C./0.1 mm). The residue was poured into 1 N sodium hydroxide (300 mL) and extracted with ethyl acetate (2×, 300 mL). The combined organic layer was washed with water (2×, 300 mL) and brine (300 mL). The ethyl acetate layer was dried over anhydrous magnesium sulfate, filtered, and the solvent removed under vacuum to give 5.1 g of crude red oil. Purification by chromatography (500 g silica gel, ethyl acetate: 2 M $NH_3$ in methanol, 20:1) afforded 3.54 g (89.3%) of a red semi-solid, mp 33–60° C.; MS EI m/e 287 (M$^+$).

Elemental analysis for $C_{15}H_{17}N_3O_3$: Calc'd: C, 62.71; H, 5.96; N, 14.62; Found: C, 62.64; H, 6.04; N, 14.23

Using this general procedure and utilizing 2-(2-chloroethoxy)-6-nitro-phenylamine or 2-(3-bromo-propoxy)-6-nitro-phenylamine or 4-chloro-2-(2-chloro-ethoxy)-6-nitro-phenylamine and benzylamine, 4-methyl-benzylamine, 1-naphthalene-methylamine, 4-tert-butyl-benzylamine, thiophene-2-methyl-amine, 4-chloro-benzylamine, thiophene-3-methylamine or 1,2,3,4-tetrahydroisoquinoline afforded:

2b 2-[2-(4-Methyl-benzylamino)-ethoxy]-6-nitro-phenylamine as a yellow solid (89%), mp 55–57° C.; EI m/e 301 (M$^+$).

Elemental analysis for $C_{16}H_{19}N_3O_3$: Calc'd: C, 62.71; H, 5.96; N, 14.62; Found: C, 62.64; H, 6.04; N, 14.23

2c 2-(3-Benzylamino-propoxy)-6-nitro-phenylamine as a viscous orange oil (85.5%); MS El m/e 301 (M$^+$).

Elemental analysis for $C_{16}H_{19}N_3O_3$: Calc'd: C, 63.77; H, 6.36; N, 13.94; Found: C, 63.66; H, 6.28; N, 13.89

2d 2-{2-[(Naphthalen-1-ylmethyl)-amino]-ethoxy}-6-nitro-phenylamine as a yellow solid (76.3%), mp 66–67° C.; MS EI m/e 337 (M$^+$).

Elemental analysis for $C_{19}H_{19}N_3O_3$: Calc'd: C, 67.64; H, 5.68; N, 12.45; Found: C, 67.20; H, 5.66; N, 12.26

2e 2-[2-(4-tert-Butylbenzylamino)-ethoxy]-6-nitro-phenylamine as an orange viscous oil (83.3%); MS EI m/e 343 (M$^+$) which analyzed as the quarter hydrate.

Elemental analysis for $C_{19}H_{25}N_3O_3 \cdot 0.25 H_2O$: Calc'd: C, 65.59; H, 7.39; N, 12.07; Found: C, 65.89; H, 7.20; N, 11.94

2f 2-[2-(4-Chloro-benzylamino)-ethoxy]-6-nitro-phenylamine as an orange solid (87.8%), mp 61–62° C.; MS EI m/e 322/324 (M$^+$) which analyzed as the quarter hydrate.

Elemental analysis for $C_{15}H_{16}N_3O_3 \cdot 0.25 H_2O$: Calc'd: C, 55.22; H, 5.10; N, 12.88; Found: C, 55.27; H, 4.96; N, 12.88

2g 2-(2-Benzylamino-ethoxy)-4-chloro-6-nitro-phenylamine as a orange-brown colored solid (54.0%), mp 87–88° C.; MS EI m/e 321/323 (M$^+$).

Elemental analysis for $C_{15}H_{16}ClN_3O_3$: Calc'd: C, 55.99; H, 5.01; N, 13.06; Found: C, 55.85; H, 4.90; N, 13.13

2h 4-Chloro-2-nitro-6-{2-[(thiophen-2-ylmethyl)-amino]-ethoxy}-phenylamine as a yellow solid (44.0%), mp 74–75° C.; MS EI m/e 327/329 (M$^+$).

Elemental analysis for $C_{13}H_{14}ClN_3O_2S$: Calc'd: C, 47.67; H, 4.33; N, 12.75; Found: C, 47.54; H, 4.11; N, 13.06

2i 4-Chloro-2-nitro-6-{2-[(thiophen-3-ylmethyl)-aminol-ethoxy}-phenylamine as a yellow solid (33.3%), mp 77–78° C.; MS EI m/e 327/329 (M$^+$).

Elemental analysis for $C_3H_{14}ClN_3O_2S$: Calc'd: C, 47.67; H, 4.33; N, 12.75; Found: C, 47.54; H, 4.18; N, 12.80

2j 2-[2-(3,4-Dihydro-1H-isoquinolin-2-yl)-ethoxy]-6-nitro-phenylamine as a yellow solid (87.1%), mp 95–97° C.; MS EI m/e 313 (M$^+$).

Elemental analysis for $C_{17}H_{19}N_3O_2$: Calc'd: C, 65.16; H, 6.11; N, 13.41; Found: C, 64.87; H, 6.11; N, 13.40

INTERMEDIATE 3a

N-[2-(2-Amino-3-nitro-phenoxy)-ethyl]-N-benzyl-2,2,2-trifluoro-acetamide

To a solution of 2-(2-benzylamino-ethoxy)-6-nitro-phenylamine (2a, 0.5 g, 1.74 mmol) and triethylamine (0.32 mL, 3.48 mmol) in anhydrous methylene chloride (10 mL) at 23° C. was added trifluoroacetic anhydride (0.32 mL, 2.26 mmol). After 2 hr the reaction was diluted with ether and washed with saturated sodium bicarbonate (3×80 mL) and the organic layer dried over anhydrous magnesium sulfate. Filtration and evaporation of the solvent gave 0.55 g (81.7%) of yellow solid, mp 134–135° C.; MS EI m/e 383 (M$^+$).

Elemental analysis for $C_{17}H_{16}F_3N_3O_4$: Calc'd: C, 53.27; H, 4.21; N, 10.96; Found: C, 53.09; H, 4.35; N, 10.93.

This general procedure utilizing 2-[2-(4-methyl-benzylamino)-ethoxy]-6-nitro-phenylamine, 2-(3-benzylamino-propoxy)-6-nitro-phenylamine, 2-{2-[(naphthalen-1-ylmethyl)-amino]-ethoxy}-6-nitro-phenylamine, 2-[2-(4-tert-butylbenzylamino)-ethoxy]-6-nitro-phenyl-amine, 2-[2-(4-chloro-benzylamino)-ethoxy]-6-nitro-phenylamine, 2-(2-benzylamino-ethoxy)-4-chloro-6-nitro-phenylamine, 4-chloro-2-nitro-6-{2-[(thiophen-2-ylmethyl)-amino]-ethoxy}-phenylamine, 4-chloro-2-nitro-6-{2-[(thiophen-3-ylmethyl)-amino]-ethoxy}-phenylamine afforded:

3b N-[2-(2-Amino-3-nitro-phenoxy)-ethyl]-2,2,2-trifluoro-N-(4-methyl-benzyl) acetamide as a yellow solid (79%), mp 172–173° C.; MS EI m/e 397 (M$^+$).

Elemental analysis for $C_{18}H_{18}F_3N_3O_4$: Calc'd: C, 54.41; H, 4.57; N, 10.58; Found: C, 54.34; H, 4.33; N, 10.53

3c N-[3-(2-Amino-3-nitro-phenoxy)-propyl]-N-benzyl-2,2,2-trifluoro-acetamide as a yellow solid (67.8%), mp 92–93° C.; MS EI m/e 397 (M$^+$).

Elemental analysis for $C_{18}H_{18}F_3N_3O_4$: Calc'd: C, 54.41; H, 4.57; N, 10.58; Found: C, 54.30; H, 4.50; N, 10.50

3d N-[2-(2-Amino-3-nitro-phenoxy)-ethyl]-2,2,2-trifluoro-N-naphthalen-1-ylmethyl-acetamide as a yellow-orange colored solid (75.3%), mp 133–135° C.; MS EI m/e 433 (M$^+$).

Elemental analysis for $C_{21}H_{18}F_3N_3O_4$: Calc'd: C, 58.20; H, 4.19; N, 9.70; Found: C, 58.28; H, 4.07; N, 9.48

3e N-[2-(2-Amino-3-nitro-phenoxy)-ethyl]-N-(4-tert-butyl-benzyl)-2,2,2-trifluoro-acetamide as a yellow solid (82.0%), mp 80–82° C.; MS EI m/e 439 (M$^+$).

Elemental analysis for $C_{21}H_{24}F_3N_3O_4$: Calc'd: C, 57.40; H, 5.51; N, 9.56; Found: C, 57.09; H, 5.31; N, 9.40

3f N-[2-(2-Amino-3-nitro-phenoxy)-ethyl]-N-(4-chloro-benzyl)-2,2,2-trifluoro-acetamide as a yellow solid (84.0%), mp 138–139° C.; MS (+)FAB m/e 418/420 (M+H)$^+$.

Elemental analysis for $C_{17}H_{15}ClF_3N_3O_4$: Calc'd: C, 48.88; H, 3.62; N, 10.06; Found: C, 48.66; H, 3.47; N, 9.82

3g N-[2-(2-Amino-5-chloro-3-nitro-phenoxy)-ethyl]-N-benzyl-2,2,2-trifluoro-acetamide as a yellow solid (67.9%), mp 106–108° C.; MS (+)FAB m/e 418/420 (M+H)$^+$.

Elemental analysis for $C_{17}H_{15}ClF_3N_3O_4$: Calc'd: C, 48.88; H, 3.62; N, 10.06; Found: C, 48.96; H, 3.50; N, 10.03

3h N-[2-(2-Amino-5-chloro-3-nitro-phenoxy)-ethyl]-2,2,2-trifluoro-N-thiophen-2-ylmethyl-acetamide as a yellow solid (59.6%), mp 97–98° C.; MS EI m/e 423/425 (M$^+$).

Elemental analysis for $C_{15}H_{13}ClF_3N_3O_4S$: Calc'd: C, 42.51; H, 3.09; N, 9.92; Found: C, 42.37; H, 2.97; N, 9.84

3i N-[2-(2-Amino-5-chloro-3-nitro-phenoxy)-ethyl]-2,2,2-trifluoro-N-thiophen-3-ylmethyl-acetamide as a yellow solid (80.0%), mp 149–150° C.; MS EI m/e 423/425 (M$^+$).

Elemental analysis for $C_{15}H_{13}ClF_3N_3O_4S$:

Calc'd: C, 42.51; H, 3.09; N, 9.92; Found: C, 42.02; H, 2.95; N, 9.78

INTERMEDIATE 4a

N-Benzyl-N-[2-(2,3-diamino-phenoxy)-ethyl]-2,2,2-trifluoro-acetamide

To a mixture of N-[2-(2-amino-3-nitro-phenoxy)-ethyl]-N-benzyl-2,2,2-trifluoro-acetamide (3a, 2.4 g, 6.26 mmol) and 10% palladium on carbon (0.40 g) in ethanol (200 mL) at 50–55° C. was added a solution of hydrazine hydrate (2.0 g) in ethanol (25 mL). The reaction was allowed to stir for 18 hr at 23° C., then the catalyst filtered through solka floc and the solvent removed under vacuum to afford 1.96 g (88.9%) of an amber-colored oil. Crystallization from ethyl acetate-hexane gave a white solid, mp 118–119° C.; MS (+)FAB m/e 354 (M+H$^+$).

Elemental analysis for $C_{17}H_{18}F_3N_3O_2$: Calc'd: C, 56.58; H, 4.72; N, 12.38; Found: C, 57.49; H, 5.10; N, 11.86

This general procedure utilizing N-[2-(2-amino-3-nitro-phenoxy)-ethyl]-2,2,2-trifluoro-N-(4-methyl-benzyl) acetamide, N-[3-(2-amino-3-nitro-phenoxy)-propyl]-N-benzyl-2,2,2-trifluoro-acetamide, N-[2-(2-amino-3-nitro-phenoxy)-ethyl]-2,2,2-trifluoro-N-naphthalen-1-ylmethyl-acetamide, N-[2-(2-amino-3-nitro-phenoxy)-ethyl]-N-(4-tert-butyl-benzyl)-2,2,2-trifluoro-acetamide, N-[2-(2-amino-3-nitro-phenoxy)-ethyl]-N-(4-chloro-benzyl)-2,2,2-trifluoro-acetamide, N-[2-(2-amino-5-chloro-3-nitro-phenoxy)-ethyl]-N-benzyl-2,2,2-trifluoro-acetamide, N-[2-(2-amino-5-chloro-3-nitro-phenoxy)-ethyl]-2,2,2-trifluoro-N-thiophen-2-ylmethyl-acetamide, and N-[2-(2-amino-5-chloro-3-nitro-phenoxy)-ethyl]-2,2,2-trifluoro-N-thiophen-3-ylmethyl-acetamide afforded:

4b N-[2-(2,3-Diamino-phenoxy)-ethyl]-2,2,2-trifluoro-N-(4-methyl-benzyl)-acetamide as a white solid (85.0%), mp 94–96° C.; MS EI m/e 367 (M$^+$).

Elemental analysis for $C_{18}H_{20}F_3N_3O_2$: Calc'd: C, 58.85; H, 5.49; N, 11.44; Found: C, 58.91; H, 5.32; N, 11.45

4c N-Benzyl-N-[3-(2,3-diamino-phenoxy)-propyl]-2,2,2-trifluoro-acetamide as a white solid (86.5%), mp 56–58° C.; MS EI m/e 367 (M$^+$).

Elemental analysis for $C_{18}H_{20}F_3N_3O_2$:

Calc'd: C, 58.85; H, 5.49; N, 11.44; Found: C, 59.00; H, 5.42; N, 11.48

4d N-[2-(2,3-Diamino-phenoxy)-ethyl]-2,2,2-trifluoro-N-naphthalen-1-ylmethyl-acetamide as a viscous yellow oil (63.0%); MS (+)FAB m/e 404 (M+H$^+$).

Elemental analysis for $C_{21}H_{20}F_3N_3O_2$: Calc'd: C, 62.53; H, 5.00; N, 10.42; Found: C, 62.45; H, 4.98; N, 10.20

4e N-(4-tert-Butyl-benzyl)-N-[2-(2,3-diamino-phenoxy)-ethyl]-2,2,2-trifluoro-acetamide as a viscous brown oil (72.7%); MS EI m/e 409 (M$^+$).

4f N-(4-Chloro-benzyl)-N-[2-(2,3-diamino-phenoxy)-ethyl]-2,2,2-trifluoro-acetamide as a brown oil (80.9%); MS EI m/e 387/389 (M$^+$).

Elemental analysis for $C_{17}H_{17}ClF_3N_3O_2$: Calc'd: C, 52.65; H, 4.42; N, 10.84; Found: C, 52.47; H, 4.51; N, 10.60

4g N-Benzyl-N-[2-(2,3-diamino-5-chloro-phenoxy)-ethyl]-2,2,2-trifluoro-acetamide as a viscous brown oil (76.2%); MS EI m/e 387/389 (M$^+$).

Elemental analysis for $C_{17}H_{17}ClF_3N_3O_2$: Calc'd: C, 52.65; H, 4.42; N, 10.84; Found: C, 52.47; H, 4.39; N, 10.90

4h N-[2-(2,3-Diamino-5-chloro-phenoxy)-ethyl]-2,2,2-trifluoro-N-thiophen-2-ylmethyl-acetamide as a viscous brown oil (71.4%); MS EI m/e 393/395 (M$^+$).

Elemental analysis for $C_{15}H_{15}ClF_3N_3O_2S$: Calc'd: C, 45.75; H, 3.84; N, 10.67; Found: C, 45.58; H, 3.93; N, 10.64

4i N-[2-(2,3-Diamino-5-chloro-phenoxy)-ethyl]-2,2,2-trifluoro-N-thiophen-3-ylmethyl-acetamide as a viscous brown oil (75.0%); MS EI m/e 393/395 (M$^+$).

Elemental analysis for $C_{15}H_{15}ClF_3N_3O_2S$: Calc'd: C, 45.75; H, 3.84; N, 10.67; Found: C, 45.39; H, 3.84; N, 10.56

INTERMEDIATE 5a

N-Benzyl-2,2,2-trifluoro-N-[2-(2-thioxo-2,3-dihydro-1H-benzoimidazol-4-yloxy)-ethyl]-acetamide A mixture of N-benzyl-N-[2-(2,3-diamino-phenoxy)-ethyl]-2,2,2-trifluoro-acetamide (0.57 g, 1.61 mmol) and 1,1'-thiocarbonyldiimidazole (0.49 g, 3.05 mmol) in anhydrous tetrahydrofuran (30 mL) was stirred at 23° C. for 2 hr. The reaction was poured into water and extracted with ethyl acetate (2×150 mL). The organic layer dried over anhydrous magnesium sulfate, filtered, and the solvent removed under vacuum. Purification by chromatography (160 g silica gel, ethyl acetate) afforded 0.54 g (85.2%) of a yellowish-colored solid. Crystallization from ethyl acetate-hexane gave a white solid, mp 158–160° C.; MS (+)FAB m/e 395 (M+H)$^+$.

Elemental analysis for $C_{18}H_{16}F_3N_3O_2S$: Calc'd: C, 54.52; H, 3.74; N, 10.56; Found: C, 54.68; H, 4.08; N, 10.63

This general procedure utilizing N-[2-(2,3-diamino-phenoxy)-ethyl]-2,2,2-trifuoro-N-(4-methyl-benzyl)-acetamide, N-benzyl-N-[3-(2,3-diamino-phenoxy)-propyl]-2,2,2-trifluoro-acetamide, N-[2-(2,3-diamino-phenoxy)-ethyl]-2,2,2-trifluoro-N-naphthalen-1-ylmethyl-acetamide, N-(4-tert-butyl-benzyl-N-[2-(2,3-diamino-phenoxy)-ethyl]-2,2,2-trifluoro-acetamide, N-(4-chloro-benzyl)-N-[2-(2,3-diamino-phenoxy)-ethyl]-2,2,2-trifluoro-acetamide, N-benzyl-N-[2-(2,3-diamino-5-chloro-phenoxy)-ethyl]-2,2,2-trifluoro-acetamide, N-[2-(2,3-diamino-5-chloro-phenoxy)-ethyl]-2,2,2-trifluoro-N-thiophen-2-ylmethyl-acetamide and N-[2-(2,3-diamino-5-chloro-phenoxy)-ethyl]-2,2,2-trifluoro-N-thiophen-3-ylmethyl-acetamide afforded:

5b 2,2,2-Trifluoro-N-(4-methyl-benzyl)-N-[2-(2-thioxo-2,3-dihydro-1H-benzoimidazol-4-yloxy)-ethyl]-acetamide as an off-white solid (90.9%), mp 195–196° C.; MS EI m/e 409 (M$^+$).

Elemental analysis for $C_{19}H_{18}F_3N_3O_2S$: Calc'd: C, 55.47; H, 4.43; N, 10.26; Found: C, 55.40; H, 4.24; N, 10.05

5c N-Benzyl-2,2,2-trifluoro-N-[3-(2-thioxo-2,3-dihydro-1H-benzoimidazol-4-yloxy)-propyl]-acetamide as a yellow foam (99.0%); MS EI m/e 409 (M$^+$) which analyzed for a three-quarter hydrate.

Elemental analysis for $C_{19}H_{18}F_3N_3O_2S$. 0.75 $H_2O$: Calc'd: C, 53.96; H, 4.65; N, 10.40; Found: C, 54.05; H, 4.49; N, 10.09

5d 2,2,2-Trifluoro-N-naphthalen-1-ylmethyl-N-[2-(2-thioxo-2,3-dihydro-1H-benzoimidazol-4-yloxy)-ethyl]-acetamide as a white solid (95.0%), mp 102–103° C.; MS EI m/e 445 (M$^+$).

Elemental analysis for $C_{22}H_{18}F_3N_3O_3S$: Calc'd: C, 58.73; H, 4.14; N, 9.34 Found: C, 58.84; H, 4.02; N, 9.17

5e N-(4-tert-Butyl-benzyl)-2,2,2-trifluoro-N-[2-(2-thioxo-2,3-dihydro-1H-benzoimidazol-4-yloxy)-ethyl]-acetamide as a white solid (86.4%), mp 199–200° C.; MS EI m/e 451 (M$^+$).

Elemental analysis for $C_{22}H_{24}F_3N_3O_2S$: Calc'd: C, 58.52; H, 5.36; N, 9.31; Found: C, 58.46; H, 5.36; N, 9.25

5f N-(4-Chloro-benzyl)-2,2,2-trifluoro-N-[2-(2-thioxo-2,3-dihydro-1H-benzoimidazol-4-yloxy)-ethyl]-acetamide as a white solid (72.0%), mp 194–196° C.; MS EI m/e 429/431 (M$^+$).

Elemental analysis for $C_{18}H_{15}ClF_3N_3O_3S$: Calc'd: C, 50.30; H, 3.52; N, 9.78; Found: C, 50.50; H, 3.54; N, 9.51

5g N-Benzyl-N-[2-(6-chloro-2-thioxo-2,3-dihydro-1H-benzoimidazol-4-yloxy)-ethyl]-2,2,2-trifluoro-acetamide as a white solid (93.8%), mp 201–202° C.

Elemental analysis for $C_{18}H_{15}ClF_3N_3O_2S$: Calc'd: C, 50.30; H, 3.52; N, 9.78; Found: C, 50.00; H, 3.40; N, 9.67

5h N-[2-(6-Chloro-2-thioxo-2,3-dihydro-1H-benzoimidazol-4-yloxy)-ethyl]-2,2,2-trifluoro-N-thiophen-2-ylmethyl-acetamide as a white solid (68.2%), mp 183–184° C.; MS EI m/e 435/437 (M$^+$).

Elemental analysis for $C_{16}H_{13}ClF_3N_3O_2S_2$: Calc'd: C, 44.09; H, 3.01; N, 9.64; Found: C, 43.76; H, 2.78; N, 9.53

5i N-2-(6-Chloro-2-thioxo-2,3-dihydro-1H-benzoimidazol-4-yloxy)-ethyl]-2,2,2-trifluoro-N-thiophen-3-ylmethyl-acetamide as a white solid (64.9%), mp 179–180° C.; MS EI m/e 435/437 (M$^+$).

Elemental analysis for $C_{16}H_{13}ClF_3N_3O_3S$: Calc'd: C, 44.09; H, 3.01; N, 9.64; Found: C, 44.11; H, 2.80; N, 9.47

INTERMEDIATE 6

3-[2-(3,4-Dihydro-1H-isoquinolin-2-yl)-ethoxy]-benzene-1,2-diamine

The general procedure used in intermediate 4 using 2-[2-(3,4-dihydro-1H-isoquinolin-2-yl)-ethoxy]-6-nitro-phenylamine (2j) afforded 3-[2-(3,4-dihydro-1H-isoquinolin-2-yl)-ethoxy]-benzene-1,2-diamine as a solid (95%), mp 76–77° C. This material was characterized as the dihydrochloride.0.4 $H_2O$ salt); MS EI m/e 283 (M$^+$).

Elemental analysis for $C_{17}H_{21}N_3O.2$ HCl.0.4 $H_2O$: Calc'd: C, 56.17; H, 6.60; N, 11.56; Found: C, 56.15; H, 6.68; N, 11.25

INTERMEDIATE 7

4-Chloro-2-(2-chloro-ethoxy)-6-nitro-phenylamine

A solution of 2-(2-chloro-ethoxy)-6-nitro-phenylamine (1a, 30.0 g, 0.14 mol), N-chlorosuccinamide and acetonitrile (1.3 L) was refluxed for 4 hr. The mixture was concentrated under vacuum and the residue was diluted with ethyl acetate (500 mL). The organic layer was washed with water (2×, 250 mL) and brine (250 mL), dried over anhydrous magnesium sulfate, filtered, and the solvent removed under vacuum to give an orange solid residue. Crystallization from ethyl acetate-hexane gave 33.5 g (95.3%) as orange solid, mp 109–110° C.; MS EI m/e 250/252/254 (M$^+$).

Elemental analysis for $C_8H_8Cl_2N_2O_3$: Calc'd: C, 38.27; H, 3.21; N, 11.16; Found: C, 38.15; H, 3.10; N, 10.96

EXAMPLE 1

4-(2-Benzylamino-ethoxy)-1,3-dihydro-benzoimidazol-2-thione

A suspension of potassium carbonate (0.90 g, 6.50 mmol) and N-benzyl-2,2,2-trifluoro-N-[2-(2-thioxo-2,3-dihydro-1H-benzoimidazol-4-yloxy)-ethyl]-acetamide (0.367 g, 0.928 mmol) in methanol-water (30 mL:2 mL) was heated to reflux for 2 hr then the solvent was evaporated and the residue dissolved in ethyl acetate (100 mL) and extracted with water (80 mL). The organic layer was dried over anhydrous magnesium sulfate, filtered, and the solvent removed under vacuum to give the crude base. Purification by chromatography (70 g silica gel, ethyl acetate:2N NH$_3$ in methanol, 20:1) afforded 0.27 g (97.2%) of a white solid. Crystallization from methanol gave white needles, mp 147–149° C.; MS m/e FAB 300 (M+H$^+$) containing methanol.

Elemental analysis for $C_{16}H_{17}N_3OS.0.75$ CH$_4$O Calc'd: C, 62.20; H, 6.23; N, 12.99; Found: C, 62.10; H, 6.07; N, 13.26

To a solution of 4-(2-benzylamino-ethoxy)-1,3-dihydro-benzoimidazole-2-thione (0.195 g, 0.65 mmol) in methanol (40 mL) was added an excess of 1N hydrogen chloride in ether to afford 0.155 g (67.4%) of the hydrochloride salt monohydrate of the tide compound as white solid, mp 253–255° C.; MS m/e (+)FAB 300 (M+H$^+$).

Elemental analysis for $C_{16}H_{17}N_3OS.HCl.H_2O$: Calc'd: C, 54.31; H, 5.70; N, 11.87; Found: C, 54.62; H, 5.48; N, 12.00

EXAMPLE 2

4-[2-(4-Methyl-benzylamino)-ethoxy]-1,3-dihydro-benzoimidazole-2-thione

The general procedure used in example 1 and utilizing 2,2,2-trifluoro-N-(4-methyl-benzyl)-N-[2-(2-thioxo-2,3-dihydro-1H-benzoimidazol-4-yloxy)-ethyl]-acetamide (5b) afforded:

4-[2-(Methyl-benzylamino)-ethoxy)]-1,3-dihydro-benzoimidazole-2-thione as a white solid quarter hydrate (97.2%), mp 154–156° C.; MS m/e EI 313 (M$^+$).

Elemental analysis for $C_{17}H_{19}N_3OS.0.25$ $H_2O$: Calc'd: C, 64.23; H, 6.18; N, 13.22; Found: C, 64.37; H, 5.93; N, 13.07.

Addition of excess 1N hydrogen chloride in ether gave 4-[2-(4-Methyl-benzylamino)-ethoxy]-1,3-dihydro-benzoimidazole-2-thione.HCl.hydrate as a white solid (71.1%), mp>250° C.; MS m/e (+)FAB 314 (M+H)$^+$.

Elemental analysis for $C_{17}H_{19}N_3OS.HCl.H_2O$ Calc'd: C, 55.50; H, 6.03; N, 11.42; Found: C, 55.81; H, 5.79; N, 11.33

EXAMPLE 3

4-(2-Benzylamino-propoxy)-1,3-dihydro-benzoimidazole-2-thione

The general procedure used in example 1 and utilizing N-benzyl-2,2,2-trifluoro-N-[3-(2-thioxo-2,3-dihydro-1H-benzoimidazole-4-yloxy)-propyl]-acetamide (5c) afforded:

4-(2-Benzylamino-propoxy)-1,3-dihydro-benzoimidazole-2-thione as a white solid (64.4%), mp 203–204° C.; MS m/e EI 313 (M$^+$).

Elemental analysis for $C_{17}H_{19}N_3OS.0.25\ H_2O$: Calc'd: C, 64.23; H, 6.18; N, 13.22; Found: C, 64.10; H, 5.08; N, 12.84

Addition of excess 1N hydrogen chloride in ether gave the hydrochloride salt quarter hydrate of 4-(2-Benzylamino-propoxy)-1,3-dihydro-benzoimidazole-2-thione as a white solid (92.5%), mp 243–244° C.; MS m/e EI 313 (M)$^+$.

Elemental analysis for $C_{17}H_{19}N_3OS.HCl.0.25\ H_2O$ Calc'd: C, 57.62; H, 5.83; N, 11.86 Found: C, 57.58; H, 5.71; N, 11.72

EXAMPLE 4

4-{2-[(Naphthalen-1-ylmethyl)-amino]-ethoxy}-1,3-dihydro-benzoimidazole-2-thione The general procedure used in example 1 and utilizing 2,2,2-trifluoro-N-naphthalen-1-ylmethyl-N-[2-(2-thioxo2, 3-dihydro-1H-benzoimidazol-4-yloxy)-ethyl]-acetamide (5d) afforded 4-{2-[(Naphthalen-1-ylmethyl)-amino]-ethoxy}-1,3-dihydro-benzoimidazole-2-thione.0.5 ethyl acetate as a white solid (66.6%), mp 191–193° C.; MS m/e EI 349 (M$^+$).

Elemental analysis for $C_{20}H_{19}N_3OS.0.5\ C_4H_8O_2$: Calc'd: C, 67.15; H, 5.89; N, 10.68; Found: C, 66.97; H, 5.75; N, 10.76

Addition of excess 1N hydrogen chloride in ether to the above product gave the three quarters hydrated hydrochloride salt of the title as a white solid (90.0%), mp 240–242° C.; MS m/e EI 349 (M)$^+$.

Elemental analysis for $C_{20}H_{19}N_3OS.HCl.0.75\ H_2O$ Calc'd: C, 60.14; H, 5.43; N, 10.52; Found: C, 60.42; H, 5.48; N, 10.09

EXAMPLE 5

4-[2-(4-tert-Butyl-benzylamino)-ethoxy]-1,3-dihydro-benzoimidazole-2-thione

The general procedure used in example 1 and utilizing N-(4-tert-butyl-benzyl)-2,2,2-trifluoro-N-[2-(2-thioxo-2,3-dihydro-1H-benzoimidazol-4-yloxy)-ethyl]-acetamide (5e) afforded:

4-[2-(4-tert-Butyl-benzylamino)-ethoxy]-1,3-dihydro-benzoimidazole-2-thione as a white solid (79.3%), mp 125–127° C.; MS m/e EI 355 (M$^+$).

Elemental analysis for $C_{20}H_{25}N_3OS$: Calc'd: C, 67.57; H, 7.09; N, 11.82; Found: C, 67.02; H, 7.00; N, 11.67

Treatment of the above free base with excess 1N hydrogen chloride in ether gave the one-uarter hydrate of the hydrochloride salt of the title compound as a white solid (90.0%), mp>250° C.; MS m/e EI 355 (M)$^+$.

Elemental analysis for $C_{20}H_{25}N_3OS.HCl.0.25\ H_2O$: Calc'd: C, 60.59; H, 6.74; N, 10.60; Found: C, 60.50; H, 5.68; N, 10.44

EXAMPLE 6

4-[2-(4-Chloro-benzylamino)-ethoxy]-1,3-dihydro-benzoimidazole-2-thione

The general procedure used in example 1 and utilizing N-(4-Chloro-benzyl)-2,2,2-trifluoro-N-[2-(2-thioxo-2,3-dihydro-1H-benzoimidazol-4-yloxy)-ethyl]-acetamide (5f) afforded:

4-[2-(4-Chloro-benzylamino)-ethoxy]-1,3-dihydrobenzoimidazole-2-thione as a white solid (85.9%), mp 160–162° C.; MS m/e (+)FAB 334/336 (M+H$^+$).

Elemental analysis for $C_{16}H_{16}ClN_3OS$: Calc'd: C, 57.57; H, 4.83; N, 12.59; Found: C, 57.17; H, 4.64; N, 12.35

Treatment with excess 1N hydrogen chloride in ether gave the hydrochloride salt of the title compound as a white solid (90.0%), mp 204–205° C.; MS m/e EI 333/335 (M)$^+$.

Elemental analysis for $C_{16}H_{16}N_3OS.HCl$: Calc'd: C, 51.90; H, 4.63; N, 11.35; Found: C, 51.86; H, 4.46; N, 11.22

EXAMPLE 7

4-(2-Benzylamino-ethoxy)-6-chloro-1,3-dihydro-benzoimidazole-2-thione

The general procedure used in example 1 and utilizing N-benzyl-N-[2-(6chloro-2-thioxo-2,3-dihydro-1H-benzoimidazol-4-yloxy)-ethyl]-2,2,2-trifluoro-acetamide (5g) afforded:

4-(2-Benzylamino-ethoxy)-6-chloro- 1,3-dihydro-benzoimidazole-2-thione as a white solid (88.2%), mp 234–237° C.; MS m/e EI 333/335 (M$^+$).

Elemental analysis for $C_{16}H_{16}ClN_3OS.0.4\ H_2O$: Calc'd: C, 56.35; H, 4.97; N, 12.32; Found: C, 56.43; H, 4.76; N, 12.26

Reaction of the above prepared compound with excess 1N hydrogen chloride in ether gave 4-(2-Benzylamino-ethoxy)-6-chloro-1,3-dihydro-benzoimidazole-2-thione.HCl as a white solid (95.0%), mp>250° C.; MS m/e EI 333/335 (M$^+$).

Elemental analysis for $C_{16}H_{16}ClN_3OS.HCl$: Calc'd: C, 51.90; H, 4.63; N, 11.35; Found: C, 51.79; H, 4.62; N, 11.20

EXAMPLE 8

6-Chloro-4-{2-[(thiophen-2-ylmethyl)-amino]-ethoxy}-1,3-dihydro-benzoimidazole-2-thione The general procedure used in example 1 and utilizing N-[2-(6-chloro-2-thioxo-2,3 dihydro-1H-benzoimidazol-4-yloxy)-ethyl]-2,2,2-tifluoro-N-thiophen-2-ylmethyl-acetamide (5h) afforded:

6-Chloro-4-{2-[(thiophen-2-ylmethyl)-amino]-ethoxy}-1,3-dihydro-benzoimidazole-2-thione.hemihydrate as a white solid (92.0%), mp 183–184° C.; MS m/e EI 339/341 (M$^+$).

Elemental analysis for $C_{14}H_{14}ClN_3OS_3$. 0.5 $H_2O$: Calc'd: C, 48.20; H, 4.33; N, 12.04; Found: C, 48.30; H, 3.99; N, 11.91

The hydrochloride salt of the tide compound was prepared as a white solid (90.0%), mp>250° C.; MS m/e (+)FAB 340 (M+H)$^+$.

Elemental analysis for $C_{14}H_{14}ClN_3OS_3.HCl$: Calc'd: C, 44.68; H, 4.02; N, 11.17; Found: C, 44.28; H, 3.87; N, 10.83

EXAMPLE 9

6-Chloro-4-{2-[(thiophen-3-ylmethyl)-amino]-ethoxy}-1,3-dihydro-benzoimidazole-2-thione The general procedure used in example 1 and utilizing N-[2-(6-chloro-2-thioxo-2,3-dihydro-1H-benzoimidazol-4-yloxy)-ethyl]-2,2,2-trifluoro-N-thiophen-3-ylmethyl-acetamide (5i) afforded:

6-Chloro-4-{2-[(thiophen-3-ylmethyl)-amino]-ethoxy}-1,3-dihydro-benzoimidazole-2-thione as a white solid (77.0%), mp 197–198° C.; MS m/e (+)FAB 340/342 (M+H$^+$).

Elemental analysis for $C_{14}H_{14}ClN_3OS_3$: Calc'd: C, 49.48; H, 4.15; N, 12.36; Found: C, 49.27; H, 4.14; N, 12.30

The hydrochloride salt of the title compound was prepared as a white solid (90.0%), mp>250° C.; MS m/e (+)FAB 340 (M+H)$^+$.

Elemental analysis for $C_{14}H_{14}ClN_3OS$·HCl: Calc'd: C, 44.68; H, 4.02; N, 11.17 Found: C, 44.28; H, 3.87; N, 10.83

EXAMPLE 10

4-[2-(3,4-Dihydro-1H-isoquinolin-2-yl)-ethoxy]-1,3-dihydro-benzoimidazole-2-thione Following the general procedure used in example 1 and utilizing 2-[2-(3,4-dihydro-1H-isoquinolin-2-yl)-ethoxy]-6-nitro-phenylamine (2j) afforded the title compound as a yellow solid (60.0%), mp 249–250° C.; MS m/e EI 325 (M$^+$).

Elemental analysis for $C_{18}H_{19}N_3OS$: Calc'd: C, 66.43; H, 5.88; N, 12.91; Found: C, 66.07; H, 5.92; N, 12.85

The hydrochloride salt of the title compound was prepared as a light yellow solid (90.0%), mp 213–214° C.; MS m/e EI 325 (M)$^+$.

Elemental analysis for $C_{16}H_{16}ClN_3OS$·HCl: Calc'd: C, 59.74; H, 5.57; N, 11.61 Found: C, 59.12; H, 5.52; N, 11.50

PHARMACOLOGY

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine D$_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given in the following table.

| Example | IC$_{50}$ (nM) D$_2$ Quin. | IC$_{50}$ (nM) D$_2$ Spiper | Ratio |
| --- | --- | --- | --- |
| 1 | 0.36 | 33.35 | 92.6 |
| 2 | 0.42 | 37.7 | 89.8 |
| 3 | 14.9 | 1191 | 79.9 |
| 4 | 0.43 | 36.9 | 85.8 |
| 5 | 0.82 | 6.87 | 8.4 |
| 6 | 0.21 | 88.0 | 409.3 |
| 7 | 0.39 | 57.0 | 139.0 |
| 8 | 0.37 | 88.0 | 237.8 |

-continued

| Example | IC$_{50}$ (nM) D$_2$ Quin. | IC$_{50}$ (nM) D$_2$ Spiper | Ratio |
| --- | --- | --- | --- |
| 9 | 0.18 | 85.0 | 472.2 |
| 10 | 2.67 | 234.0 | 87.6 |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addition, and addition to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired, The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the formula:

[Structure I: benzimidazole-2-thione with OCH2(CH2)nNR2R3 substituent and Y substituent]

I wherein:

$R^1$ is hydrogen or $C_1$–$C_6$ alkyl;

$R^2$ is hydrogen or $C_1$–$C_6$ alkyl;

$R^3$ is selected from hydrogen, straight-chain and branched alkyl group having up to 10 carbon atoms, cyclohexylmethyl and —$(CH_2)_m$Ar where Ar is phenyl, naphthyl, thienyl, furanyl or pyridinyl, each optionally substituted by one or two substituents selected independently from $C_1$–$C_6$ alkyl, halogen, $C_1$–$C_6$ alkoxy, and trifluoromethyl;

or $NR^2R^3$ is 1, 2, 3, 4-tetrahydroquinolin-1-yl, or 1, 2, 3, 4-tetrahydroquinolin-2-yl;

m is 1–5;

n is 1 or 2;

Y is halogen, $C_1$–$C_6$ alkyl or $C_1$–$C_6$ alkoxy;

or a pharmraceutcally acceptable salt thereof.

2. A compound according to claim 1 wherein $R^3$ is benzyl, substituted benzyl, thienylmethyl, furanylmethyl, phenylbutyl, or cyclohexylmethyl.

3. A compound according to claim 1 which is 4(2-benzylamino-ethoxy)-6-chloro-1,3-dihydro-benzoimidazole-2-thione or a pharmaceutically acceptable salt thereof.

4. A compound according to claim 1 which is 6-chloro-4-{2-[(thiophen-3-ylmethyl)-amino]-ethoxy}-1,3-dihydro-benzoimidazole-2-thione or a pharmaceutically acceptable salt thereof.

5. A compound according to claim 1 which is 6-Chloro-4-{2-[(thiophen-2-ylmethyl)-amino]-ethoxy}-1,3-dihydro-benzoimidazole-2-thione or a pharmaceutically acceptable salt thereof.

6. A compound of the formula:

[Structure I]

I wherein:

$R^1$ is hydrogen;

$R^2$ is hydrogen;

$R^3$ is selected from hydrogen, straight-chain and branched alkyl group having up to 10 carbon atoms, cyclohexylmethyl and $(CH_2)_m$Ar where Ar is phenyl, naphdlyl, thienyl, furanyl or pyridyl, each optionally substituted by one or two substituents selected independently from $C_1$–$C_6$ alkyl, halogen, $C_1$–$C_6$ alkoxy and trifluoromethyl:

or $NR^2R^3$ is 1, 2, 3, 4-tetrahydroquinolin-1-yl or 1, 2, 3, 4-tetrahydro-isoquinolin-2-yl;

m is 1–5;

n is 1 or 2; and

Y is hydrogen.

7. A compound according to claim 6 wherein $R^3$ is benzyl, substituted benzyl, thienylmethyl, furanylmethyl, phenylbutyl, or cyclohexylmethyl.

8. A compound according to claim 6 which is 4-(2-benzylamino-ethoxy)-1,3-dihydro-benzoimidazole-2-thione or a pharmaceutically acceptable salt thereof.

9. A compound according to claim 6 which is 4-[2-(4-methyl-benzyl)-amino-ethoxy]-1,3-dihydro-benzoimidazole-2-thione or a pharmaceutically acceptable salt thereof.

10. A compound according to claim 6 which is 4-(2-benzylamino-propoxy) 1,3-dihydro-benzoimidazole-2-thione or a pharmaceutically acceptable salt thereof.

11. A compound according to claim 6 which is 4-{2-[(naphthalen-1-ylmethyl)-amino]-ethoxy}-1,3-dihydro-benzoimidazole-2-thione or a pharmaceutically acceptable salt thereof.

12. A compound according to claim 6 which is 4-[2-(4-tert-butyl-benzylamino)-etboxy]-1,3-dihydro-benzoimidazole-2-thione or a pharmaceutically acceptable salt thereof.

13. A compound according to claim 6 which is 4-[2-(4-chloro-benzylamino)-ethoxy]-1,3-dihydro-benzoimidazole-2-thione or a pharmaceutically acceptable salt thereof.

14. A compound which is 4-[2-(3,4 Dihydro 1H-isoquinolin-2-yl)-ethoxy]-1,3-dihydro-benzoimidazole-2-thione or a pharmaceutically acceptable salt thereof.

15. A pharmaceutical composition comprising a pharmaceutically acceptable carrier and a therapeutically effective amount or a compound of the formula

[Structure I]

I wherein:

$R^1$ is hydrogen or $C_1$–$C_6$ alkyl;

$R^2$ is hydrogen or $C_1$–$C_6$ alkyl;

$R^3$ is selected from hydrogen, straight-chain and branched alkyl group having up to 10 carbon atoms, cyclohexylmethyl and —$(CH_2)_m$Ar where Ar is phenyl, naphthyl, thienyl, furanyl or pyridinyl, each optionally substituted by one or two substituents selected independently from $C_1$–$C_6$alkyl, halogen, $C_1$–$C_6$ alkoxy, and trifluoromethyl, or $NR^2R^3$ is 1, 2, 3, 4-tetrahydroquinolin-1-yl, or 1, 2, 3, 4-tetrahydroisquinolin-2-yl;

m is 1–5;

n is 1 or 2,

Y is halogen, $C_1$–$C_6$ alkyl or $C_1$–$C_6$ alkoxy; or a pharmaceutically acceptable salt thereof.

16. A pharmaceutical composition comprising a pharmaceutically acceptable carrier and a therapeutically effective amount of a compound of claim 6.

17. A method of treating diseases in a mammal that respond to treatment with a dopamine $D_2$ agonist which comprises administration to a mammal in need thereof a therapeutically effective amount of a compound of the formula

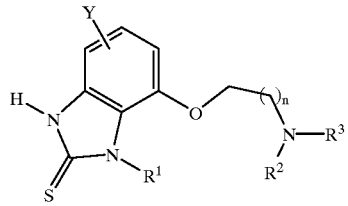

wherein:
- $R^1$ is hydrogen or $C_1$–$C_6$ alkyl;
- $R^2$ is hydrogen or $C_1$–$C_6$ alkyl;
- $R^3$ is selected from hydrogen, straight-chain and branched alkyl group having up to 10 carbon atoms, cyclohexylmethyl and —$(CH_2)_m$Ar where Ar is phenyl, naphthyl, thienyl, furanyl or pyridinyl, each optionally substituted by one or two substituents selected independently from $C_1$–$C_6$ alkyl, halogen, $C_1$–$C_6$ alkoxy, and trifluoromethyl,
  or $NR^2R^3$ is 1, 2, 3, 4-terrahydroquinolin-1-yl, or 1, 2, 3, 4-tetrahydroisoquinolin-2-yl;
- m is 1–5;
- n is 1 or 2;
- Y is halogen, $C_1$–$C_6$ alkyl or $C_1$–$C_6$ alkoxy;

or a pharmaceutically acceptable salt thereof.

18. The method according to claim 17 wherein the disease treated is schizophrenia.

19. The method according to claim 17 wherein the disease treated is Tourette's syndrome.

20. The method according to claim 17 wherein the disease treated Parkinson's disease.

21. The method according to claim 17 wherein the disease treated is drug or alcohol addiction.

22. A method of treating diseases in a mammal that responds to treatment with a dopamine $D_2$ agonist which comprises administration to a mammal in need thereof a therapeutically effective amount of a compound of the formula:

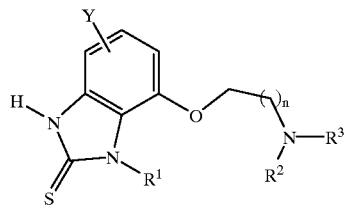

wherein:
- $R^1$ is hydrogen;
- $R^2$ is hydrogen;
- $R^3$ is selected from hydrogen, straight-chain and branched alkyl group having up to 10 carbon atoms, cyclohexylmethyl and —$(CH_2)_m$Ar where Ar is phenyl, naphthyl, thienyl, furanyl or pyridyl, each optionally substituted by one or two substituents selected independently from $C_1$–$C_6$ alkyl, halogen, $C_1$–$C_6$ alkoxy and trifluoromethyl;
  or $NR^2R^3$ is 1, 2, 3, 4-tetrahydroquinolin-1-yl or 1, 2, 3, 4-tetrahydro-isoquinolin-2-yl;
- m is 1–5;
- n is 1 or 2; and
- Y is hydrogen.

23. The method according to claim 22 wherein the disease treated is schizophrenia.

24. The method according to claim 22 wherein the disease treated is Tourette's syndrome.

25. The method according to claim 22 wherein the disease treated Parkinson's disease.

26. The method according to claim 22 wherein the disease treated is drug or alcohol addiction.

* * * * *